(12) United States Patent
Takahashi et al.

(10) Patent No.: US 9,950,094 B2
(45) Date of Patent: Apr. 24, 2018

(54) LAYERED CELL SHEETS CONTAINING MYOBLASTS AND METHOD FOR PRODUCING SAME

(71) Applicant: TOKYO WOMEN'S MEDICAL UNIVERSITY, Tokyo (JP)

(72) Inventors: Hironobu Takahashi, Tokyo (JP); Tatsuya Shimizu, Tokyo (JP); Teruo Okano, Tokyo (JP)

(73) Assignee: Tokyo Women's Medical University, Tokyo (JP)

( * ) Notice: Subject to any disclaimer, the term of this patent is extended or adjusted under 35 U.S.C. 154(b) by 81 days.

(21) Appl. No.: 14/778,590

(22) PCT Filed: Mar. 11, 2014

(86) PCT No.: PCT/JP2014/056363
§ 371 (c)(1),
(2) Date: Sep. 19, 2015

(87) PCT Pub. No.: WO2014/148321
PCT Pub. Date: Sep. 25, 2014

(65) Prior Publication Data
US 2016/0279292 A1 Sep. 29, 2016

(30) Foreign Application Priority Data
Mar. 19, 2013 (JP) ................ 2013-057282

(51) Int. Cl.
| | | |
|---|---|---|
| *C12N 5/00* | (2006.01) | |
| *A61L 27/36* | (2006.01) | |
| *C12N 5/077* | (2010.01) | |
| *A61L 27/16* | (2006.01) | |

(52) U.S. Cl.
CPC ........... *A61L 27/367* (2013.01); *A61L 27/16* (2013.01); *C12N 5/0658* (2013.01); *A61L 2430/30* (2013.01); *C12N 2502/081* (2013.01); *C12N 2502/28* (2013.01); *C12N 2513/00* (2013.01); *C12N 2533/30* (2013.01); *C12N 2533/54* (2013.01); *C12N 2535/10* (2013.01)

(58) Field of Classification Search
CPC ..... C12N 5/0619; C12N 5/0658; C12N 5/069
See application file for complete search history.

(56) References Cited

U.S. PATENT DOCUMENTS

| | | | |
|---|---|---|---|
| 2007/0092492 A1 | 4/2007 | Matsuda et al. | |
| 2010/0216242 A1* | 8/2010 | Shimizu ................. | C12M 23/20 435/396 |
| 2012/0052524 A1* | 3/2012 | Kinooka ................ | C12Q 1/025 435/29 |
| 2012/0156781 A1 | 6/2012 | Takahashi et al. | |
| 2015/0110756 A1 | 4/2015 | Matsuda et al. | |

FOREIGN PATENT DOCUMENTS

| | | |
|---|---|---|
| JP | 2012-105587 A | 6/2012 |
| JP | 2012-139541 A | 7/2012 |
| JP | 2012-165730 A | 9/2012 |
| WO | WO 2010-101225 A1 | 9/2010 |
| WO | WO 2011-024963 A1 | 3/2011 |
| WO | WO 2011-046104 A1 | 4/2011 |

OTHER PUBLICATIONS

Altomare et al., *Acta Biomaterialia*, 6: 1948-1957 (2010).
Bian et al., *Biomaterials*, 30: 1401-1412 (2009).
Choi et al., *Biomaterials*, 29: 2899-2906 (2008).
Haraguchi et al., *Biomaterials*, 27: 4765-4774 (2006).
Haraguchi et al., *Nature Protocols*, 7(5): 850-858 (2012).
Hosseini et al., *Tissue Engineering: Part A*, 18(23-24): 2453-2465 (2012).
Kino-Oka et al., *J. Biosci. Bioeng.*, 113(1): 128-131 (2012).
Lam et al., *Biomaterials*, 27: 4340-4347 (2006).
Matsumoto et al., "Alignment Control of Myoblast in Highly Oriented Hydrogel," *The Journal of the Japanese Society for Dental Materials and Devices*, 25(2): 89, item A-11 (Apr. 5, 2006).
Sasagawa et al., *Biomaterials*, 31: 1646-1654 (2010).
Sawa et al, *Surg. Today*, 42: 181-184 (2012).
Sekine et al., "Naihi-Shinkin Kyobaiyo Saibo Sheet Ishoku ni yoru Saisei Shinkin Soshikinai Kekkanmo Shinsei no Sokushin to Shinkino Kaizen Koka" ["Cardiomyocyte Sheets Co-Cultured With Endothelial Cells Improve Cardiac Function of Ischemic Heart"], *Japan Research Promotion Society for Cardiovascular Disease Heisei 18 Nendo Kenkyu Jissekishu*, 21: 5-8 (2006).
Sekine et al., "Kyoketsusei Shinfuzen ni Taisuru Naihi-Shinkin Kyobaiyo Saibo Sheet no Ishoku" ["Transplantation of Cell Sheets Comprising Co-Cultured Endothelial Cells and Cardiomyocytes to Ischemic Heart Disease"], *Dai 19 Kai Japanese Association of Cardiovascular Pharmacology Koen Yoshishu*, 19: 34, item A-II-3 (2009).
Shimizu et al., "Shinkin-Naihi Kyobaiyo Saibo Sheet o Mochiita Kekkanmo no Seigyo," Kosei Rodo Kagaku Kenkyuhi Hojokin (Hito Genome Saisei Iryo To Kenkyu Jigyo) Kan'yokei Kansaibo o Mochiita Shinkin Kekkan Saisei Ryoho no Kiso Oyobi Rinsho Kenkyu, pp. 17-18 (2006).
Takahashi et al., "Pattern-ka Ondo Otosei Baiyo Kizai o Riyo shita Haikosei o Yusuru Saibo Sheet no Sakusei" ["Fabrication of Cell Sheets with an Orientation Using Micropatterned Thermoresponsive Cell Culture Substrate"], *The Japanese Society for Regenerative Medicine Zasshi, Regenerative Medicine*, 10(special extra issue, Dai 10 Kai The Japanese Society for Regenerative Medicine Sokai Program Shoroku [The 10th Congress of the Japanese Society for Regenerative Medicine], Oral Presentation O-35-6 (Mar. 2, 2011).

(Continued)

*Primary Examiner* — Ruth A Davis
(74) *Attorney, Agent, or Firm* — Leydig, Voit & Mayer, Ltd.

(57) ABSTRACT

Provided are layered cell sheets, comprising a plurality of layered cell sheets containing myoblasts, in which each cell sheet comprises cell population containing myoblasts with controlled orientations. Preferably provided are the layered cell sheets comprising a region in which the orientations of the cell population containing the myoblasts in each cell sheet are identical to each other.

7 Claims, 4 Drawing Sheets

(56) References Cited

OTHER PUBLICATIONS

Takahashi et al., *Biomacromolecules*, 12: 1414-1418 (2011).
Takeda et al., "Electrospinning Katei de Kagaku Kakyo o Hodokoshita Haikoka Teimitsudo 'Genjo' Collagen Micro Fiber Ashiba no Sakusei to Ko Saibo Mitsudo Kinkan Soshiki no Kochiku" ["Novel String-Like Scaffold of Type I Collagen Simultaneously Crosslinked with Glutaraldehyde in Electrospinning Process and Fabrication of Oriented 3D Myotube Tissue"], *The 93rd Annual Meeting of the Chemical Society of Japan in Spring* (2013) *Koen Yokoshu*, p. 892, item 4 D4-38 (Mar. 8, 2013).
Zhao et al., *Biotech. Bioeng.*, 102: 624-631 (2009).
Japanese Patent Office, International Search Report in International Patent Application PCT/JP2014/056363 (dated Jun. 10, 2014).
Masuda et al., *Advanced Drug Delivery Reviews*, 60(2): 277-285 (2008).
Nagamori et al., *Biomaterials*, 34(3): 662-668 (2013).
Sakaguchi et al., *Journal of Controlled Release*, 205: 83-88 (2015).
Takahashi et al., *Biomaterials*, 32(34): 8830-8838 (2011).
Takahashi et al., *Biomaterials*, 34(30): 7372-7380 (2013).
Takahashi et al., "Construction of Cell Sheet-based 3D Tissues with Designed Cell Orientation using Anisotropic Cell Sheets," 2014 International Symposium on Micro-Nanomechatronics and Human Science (MHS), pp. 1-3 (Nov. 10, 2014).
European Patent Office, Extended European Search Report in Patent Application No. 14767404.8 (dated Sep. 29, 2016).
The International Bureau of WIPO, International Preliminary Report on Patentability in International Patent Application PCT/JP2014/056363 (dated Oct. 1, 2015).

\* cited by examiner culture in growth media culture in differentiation media

LAYERED CELL SHEETS CONTAINING MYOBLASTS AND METHOD FOR PRODUCING SAME

CROSS-REFERENCE TO RELATED APPLICATIONS

This patent application is the U.S. national phase of International Patent Application No. PCT/JP2014/056363, filed Mar. 11, 2014, which claims the benefit of Japanese Patent Application No. 2013-057282, filed on Mar. 19, 2013, which are incorporated by reference in their entireties herein.

TECHNICAL FIELD

The present invention relates to layered cell sheets containing myoblasts useful in fields of biology, medicine, and the like, and to methods for producing the layered cell sheets.

BACKGROUND ART

Some of native tissues have the orientation of highly organized cells and/or extracellular matrices (ECMs). The orientation of aligned muscle tissues is a key factor for generating a mechanical function in native skeletal muscle having a highly organized structure comprising the parallel fascicles of muscle fibers. In the early stage of development of mature skeletal muscle, myoblasts which are precursor muscle cells are fused to form myotubes, and the newly formed myotubes are merged to be in directions parallel to each other and thereafter finally mature to muscle fibers. Accordingly, control of alignment of myoblasts is an important step for constructing muscle tissue mimicking a living body.

To date, a lot of finely processed materials have been developed for controlling the alignment of myoblasts (Non Patent Literatures 1 to 5). However, success has not been attained in biotissue engineering fields because it has been basically impossible to separate myoblasts from such surfaces subjected to fine processing. Such inseparable coupling has precluded the design of myoblast and myotube structures oriented to three dimensions.

Tissue-like cell monolayers called "cell sheets" have been developed, and the new field of tissue regeneration technology has been established. Poly(N-isopropylacrylamide) (PIPAAm) which is a thermoresponsive polymer grafted on a cell culture substrate has enabled confluent cells to be harvested without being damaged as a single cell sheet at a culture temperature allowed to be lower than 32° C. which is the lower critical solution temperature (LCST) of PIPAAm (Patent Literatures 1 and 2). Such a cell sheet can be transplanted to a damaged tissue without an additional procedure such as suture because the cell sheet associated with an entire ECM can be harvested. A myoblast sheet has been implanted for treating severe heart failure based on the technology (Non Patent Literature 6). Furthermore, biotissue engineering based on such cell sheets has enabled a 3D tissue without a scaffold to be created by layering a plurality of cell sheets (Non Patent Literatures 7 and 8). ECMs held on individual cell sheets enable the layered cell sheets to have definite layer shapes and to physically and biologically interact with each other (Non Patent Literatures 9 and 10).

Patent Literature 3 discloses a sheet-shaped three-dimensional structure for application to heart diseases, comprising myoblasts, and Patent Literature 4 discloses layered cell sheets with myoblasts or the like. In the literatures, however, the orientations of cells in each layer have not been controlled.

Non Patent Literature 7 discloses that vascular endothelial cells sandwiched between myoblast sheets are cultured. In the literature, however, the orientations of cells in each layer have not been controlled.

CITATION LIST

Patent Literature

Patent Literature 1: Japanese Patent Laid-Open No. 2012-105587
Patent Literature 2: International Publication No. WO 2011/024963
Patent Literature 3: Japanese Patent Laid-Open No. 2012-139541
Patent Literature 4: Domestic Re-publication of PCT International Publication No. 2010/101225

Non Patent Literature

Non Patent Literature 1: Biomaterials 27, 4340-4347 (2006).
Non Patent Literature 2: Biomaterials 29, 2899-2906 (2008).
Non Patent Literature 3: Biomaterials 30, 1401-1412 (2009).
Non Patent Literature 4: Biotech. Bioeng. 102, 624-631 (2009).
Non Patent Literature 5: Acta Biomater. 6, 1948-1957 (2010).
Non Patent Literature 6: Surg. Today 42, 181-184 (2012).
Non Patent Literature 7: Biomaterials 31, 1646-1654 (2010).
Non Patent Literature 8: Nat. Protoc. 7, 850-858 (2012).
Non Patent Literature 9: Biomaterials 27, 4765-4774 (2006).
Non Patent Literature 10: J. Biosci. Bioeng. 113, 128-131 (2012).

SUMMARY OF INVENTION

The present invention is intended to solve such conventional problems as described above, and is directed at providing layered cell sheets comprising myoblasts with controlled orientations and at providing a method for producing the layered cell sheets.

The present inventors performed extensive studies in order to solve the above-described problems. As a result, it has become possible to construct a three-dimensional myotube construct with desired orientation by layering cell sheets comprising myoblasts with controlled orientations (hereinafter referred to as cell sheets containing myoblasts, or also simply referred to as myoblast sheets). In addition, it was found that a cell sheet with controlled orientation layered over another cell sheet can change the cell orientation of layered cell sheets underneath the cell sheet in production of the layered cell sheets comprising myoblasts. As a result, layered cell sheets comprising myoblasts with orientations that are fully coincident with each other are produced, whereby myoblasts and a myotube construct oriented to three dimensions can be created. Furthermore, the inventors also succeeded in production of layered cell sheets comprising vascular endothelial cells or nerve cells with orientations identical to those of cell population comprising myoblasts between cell sheets containing the cell population comprising the myoblasts with controlled orientations. The present invention was accomplished based on such findings.

The present invention provides the followings:

Item 1. Layered cell sheets, comprising a plurality of layered cell sheets containing myoblasts, wherein each cell sheet comprises cell population containing myoblasts with controlled orientations.

Item 2. The layered cell sheets according to Item 1, comprising a region in which orientations of the cell population containing the myoblasts in each cell sheet are identical to each other.

Item 3. The layered cell sheets according to Item 2, wherein the layered cell sheets comprise vascular endothelial cells or nerve cells with orientations identical to those of the cell population containing the myoblasts between the cell sheets comprising the cell population containing the myoblasts.

Item 4. The layered cell sheets according to any one of Items 1 to 3, wherein each cell sheet comprising the cell population containing the myoblasts is obtained by culturing the myoblasts on a thermoresponsive polymer-coated substrate and by detaching the myoblasts from the substrate.

Item 5. The layered cell sheets according to any one of Items 1 to 4, wherein a percentage of the myoblasts in each cell sheet is 50% or more.

Item 6. A method for producing layered cell sheets, comprising a step of layering a second cell sheet comprising cell population containing myoblasts with random orientations on a first cell sheet comprising cell population containing myoblasts with controlled orientations, and thereby obtaining layered cell sheets which comprise a region in which orientations of cell population containing myoblasts in each cell sheet are identical to each other.

Item 7. A method for producing layered cell sheets comprising myoblasts and vascular endothelial cells or nerve cells; said method comprising a step of forming a layer of vascular endothelial cells or nerve cells on a first cell sheet comprising cell population containing myoblasts with controlled orientations and layering a second cell sheet comprising myoblasts thereon, and thereby obtaining layered cell sheets which comprise a region in which an orientation of a cell group comprising myoblasts and an orientation of vascular endothelial cells or nerve cells in each cell sheet are identical to each other.

Item 8. A method for producing layered cell sheets, comprising a step of placing, underneath a first cell sheet comprising cell population containing myoblasts with controlled orientations, a second cell sheet comprising cell population containing myoblasts with orientations different from the orientations in the first cell sheet comprising the myoblasts, and thereby obtaining layered cell sheets which comprise a region in which orientations of cell population containing myoblasts in each cell sheet are identical to each other.

Advantageous Effects of Invention

The layered cell sheets comprising myoblasts of the present invention facilitates formation of a myotube, and application of the layered cell sheets to fields of biology, medicine, regenerative medicine, and the like can be expected, because the layered cell sheets have each layer of which the orientation is controlled.

It is considered that it is necessary that the orientations of a regenerated muscle tissue are uniform in a manner similar to those in the case of the living body in order for the regenerated muscle tissue to exert muscular strength equivalent to that of a muscle tissue in the living body. From this viewpoint, the layered cell sheets with controlled orientations of the present invention can be efficiently engrafted into a living body in a short time, and can be preferably used in regenerative medicine to completely recover the function of a damaged site.

DESCRIPTION OF EMBODIMENTS

Figure 1:
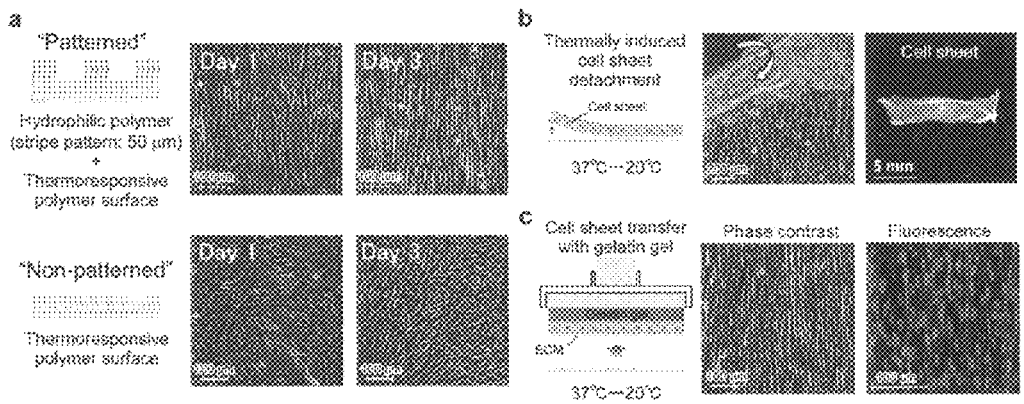
FIG. 1 shows views illustrating control of alignment of myoblasts in which a patterned thermoresponsive cell culture substrate is used, and detachment of an aligned myoblast sheet. (a) A schematic view of a patterned surface or a non-patterned surface, and photographs illustrating the results of culturing myoblasts from human skeletal muscle on the patterned surface or the non-patterned surface. (b) A schematic view and a photograph illustrating detachment of an aligned myoblast sheet, and a photograph of the cell sheet shrinking after the detachment (the original size of the adherent cell sheet was 20×20 mm). (c) A schematic view of a step of collecting a myoblast sheet adhering to a gelatin gel from a substrate surface, and photographs illustrating the results of culturing the transferred cell sheet. The aligned orientations of the cell sheet were maintained even 3 weeks after the transfer of the cell sheet. The fluorescence image shows that actin filaments and nuclei are also well aligned.

The layered cell sheets of the present invention are layered cell sheets comprising a plurality of layered cell sheets containing myoblasts, wherein each cell sheet comprising cell population containing myoblasts has controlled orientation.

Such a myoblast is preferably a skeletal myoblast and is characterized by expression of a marker gene such as CD56, MyoD or myogenin. The myoblast which is a material for a cell sheet containing myoblasts may be isolated, or may be obtained by differentiation of a stem cell. The myoblast is preferably derived from a mammal, more preferably from a human.

In the present invention, as long as the cell sheet comprising cell population containing myoblasts contains myoblasts, another cell such as a fibroblast may coexist in the cell sheet. It is preferable that 50% of all the cells of the cell sheet are composed of myoblasts. More preferably 60% or more, still more preferably 70% or more, particularly preferably 80% or more, and most preferably 90% or more of all the cells of the cell sheet are composed of myoblasts.

"Controlled orientation" means that cells are placed according to a regular pattern, and preferably means that cells are unidirectionally aligned and placed.

In the layered cell sheets containing myoblasts of the present invention, the orientations (alignment directions) of myoblasts may be different between sheets, as in a case in which, for example, a second sheet has an orientation orthogonal to a first sheet. The layered cell sheets preferably have a region in which the orientations (alignment directions) of cell population containing myoblasts in each sheet are identical to each other.

The number of the layered cell sheets containing myoblasts is preferably 2 to 10, more preferably 2 to 6, more preferably 2 to 4. The thickness of the layered sheets is, for example, 10 μm to 100 μm, preferably 10 μm to 20 μm. The size of each sheet depends on a transplantation site and an application, and is not particularly limited.

Part or the whole of the cell sheet containing myoblasts may be differentiated to form myosin heavy chain positive myotubes. In this case, the differentiated cell sheets may be layered, or the layered cell sheets may be differentiated.

A method for producing layered cell sheets containing myoblasts of the present invention is not particularly limited. The layered cell sheets can be obtained by culturing cell population containing myoblasts on a thermoresponsive polymer-coated substrate having a patternized surface, to produce cell sheets containing myoblasts with controlled orientations, detaching the cell sheets from the substrate, and then layering the cell sheets.

A preferred method for producing a cell sheet containing myoblasts will be described below.

The cell sheet containing myoblasts is produced by, for example, a method comprising: a) a step of culturing a cell population containing myoblasts on a thermoresponsive polymer-coated substrate having a patterned surface, to form a cell sheet containing myoblasts on the substrate; and b) a step of detaching the cell sheet containing the myoblasts at culture temperature below the lower critical solution temperature of a thermoresponsive polymer thereof.

The thermoresponsive polymer is preferably a thermoresponsive polymer which shows a change in hydration force at 0 to 80° C. Examples of such thermoresponsive polymers include polymers having a lower critical solution temperature (LCST) and polymers having an upper critical solution temperature (UCST). One or more kinds of the polymers are available.

Specific examples thereof include poly-N-isopropylacrylamide (PIPAAm), poly-N-n-propylacrylamide, poly-N-n-propylmethacrylamide, poly-N-ethoxyethylacrylamide, poly-N-tetrahydrofurfurylacrylamide, poly-N-tetrahydrofurfurylmethacrylamide, and poly-N,N-diethylacrylamide, especially PIPAAm, poly-N-n-propylmethacrylamide, and poly-N,N-diethylacrylamide can be preferably used, and PIPAAm can be particularly preferably used. PIPAAm has a lower critical solution temperature of around 32° C., and therefore, in this case, a cell sheet can be easily produced by changing the temperature from the ordinary culture temperature (for example around 37° C.) of culture liquid to around 20° C.

The thermoresponsive polymer may be a homopolymer or a copolymer. Examples of such polymers include polymers described in Japanese Patent Laid-Open No. 2-211865, as well as the above. Specifically, such polymers are obtained, for example, by homopolymerization or copolymerization of monomers described below. Examples of the monomers that can be used include (meth)acrylamide compounds, N- (or N,N-di)alkyl-substituted (meth)acrylamide derivatives, or vinyl ether derivatives, and for copolymers, any two or more of them can be used. Furthermore, copolymerization with monomers other than the above-described monomers, graft or copolymerization of polymers with each other, or mixtures of homopolymers and copolymers may be used. Crosslinking is also possible as long as the original properties of the polymers are not deteriorated.

The film thickness of the thermoresponsive polymer layer coated on the substrate is not particularly limited if enabling exertion of thermoresponsibility, and is preferably within a range of 0.5 nm to 300 nm, and more preferably within a range of 1 nm to 100 nm.

The substrate is not particularly limited if being able to support the above-described stimulus-responsive layer and a cell adhesion inhibition layer. Examples of such substrates include polyethylene terephthalate (PET), polystyrene (PS), polycarbonate (PC), TAC (triacetylcellulose), polyimide (PI), nylon (Ny), low density polyethylene (LDPE), medium density polyethylene (MDPE), vinyl chloride, vinylidene chloride, polyphenylene sulfide, polyethersulfone, polyethylene naphthalate, polypropylene, acrylic materials such as urethane acrylate, cellulose, glass, modified glass, and ceramics. A biodegradable polymer such as polylactic acid, polyglycolic acid, polycaprolactone, or a copolymer thereof is also acceptable. The substrate may also be porous. The above-described thermoresponsive layer in itself may also be used as the substrate.

The thickness of the substrate, which is not particularly limited if enabling the above-described stimulus-responsive layer or the like to be stably supported, is, for example, within a range of 10 μm to 1000 μm, preferably within a range of 50 μm to 200 μm.

A method for coating the substrate with the thermoresponsive polymer is not particularly limited but may be, for example, a method described in Japanese Patent Laid-Open No. 2-211865. In other words, the coating of the substrate with the above-described monomer or polymer can be performed by any of electron beam irradiation (EB), γ-ray irradiation, ultraviolet ray irradiation, plasma treatment, corona treatment, and organic polymerization reaction; physical adsorption such as application or contact; or the like.

As the shape of the thermoresponsive layer, a shape allowing the entire surface of the above-described substrate to be coated is usually used, and formation of a pattern form on the above-described substrate is preferred for controlling the orientations of myoblasts. In the case of forming the above-described thermoresponsive layer in a pattern form on the above-described substrate, there can be used a method of forming a coating film of the above-described thermoresponsive material composition and then performing patterning by a photolithographic method, or a method of applying the above-described thermoresponsive material composition in a pattern form using a pattern printing method such as gravure printing, flexographic printing, screen printing, or an inkjet method.

The thermoresponsive layer can be subjected to surface treatment, as needed. This is because various functions can be given depending on the kind of the surface treatment. Examples of the surface treatment include hydrophilic treatment such as silane treatment. This is because the pattern form of the exposed surface of the thermoresponsive layer can be precisely formed by the hydrophilic treatment such as the silane treatment. Accordingly, micro-patterned myoblasts with a desired pattern can be more reliably obtained.

As the silane treatment, for example, a silane coupling agent can be used. Examples of the silane coupling agent include methacryloxysilanes, vinylsilanes, aminosilanes, and epoxysilanes, and especially, methacryloxysilanes can be preferably used. Examples of methods for applying silane coupling agents include a method of dissolving a silane coupling agent in an organic solvent in which the above-described silane coupling agents can be dissolved, and of applying the solution to the above-described stimulus-responsive layer by a common application method, e.g., a spinner method, a die coat method, an immersion method, a gravure printing method, CVD (chemical vapor deposition method), or the like. For example, in the case of the spinner method, conditions can be set at 700 rpm to 2000 rpm and at around 3 seconds to 20 seconds.

Myoblasts are cultured on a thermoresponsive polymer-coated substrate produced as described above. The temperature of a medium is not particularly limited if in a case in which the polymer coated on the surface of the substrate has an upper critical solution temperature, the temperature is not more than the upper critical solution temperature, or if in a case in which the polymer has a lower critical solution temperature, the temperature is not less than the lower critical solution temperature. However, it will be appreciated that culture in a low-temperature range in which cultured cells are prevented from growing or in a high-temperature range in which cultured cells die is inappropriate. For culture conditions other than temperature, which are not particularly limited, technologies well known in the art can be used. For example, a medium may be a medium to which a serum such as known fetal calf serum (FCS) is added, or a serum-free medium to which such a serum is not added. Culture time may be set according to the purpose of use of cell sheets containing myoblasts.

As a medium for culturing myoblasts, which is not particularly limited if a medium commonly used for myoblasts is used, a known medium can be used. However, it is desirable that the components of the medium used are components of which the origins are clear or components approved for medicaments when cell sheets containing an obtained layered myoblasts are used for therapy on humans.

Use of a differentiation-inducing medium is preferred for differentiation of myoblasts into muscle tissue. Examples of the differentiation-inducing medium include media containing horse serum.

For detaching and collecting cell sheets containing cultured myoblasts from a substrate material, the cell sheets containing the cultured myoblasts or the cell sheets attached to the polymer film can be detached by allowing the temperature of the substrate material to which the cells adhere to be not less than the upper critical solution temperature of the coating polymer of the substrate or not more than the lower critical solution temperature of the substrate. The cell sheets containing the myoblasts can be detached in a culture liquid in which the cells have been cultured or in another isocratic liquid, and such a liquid can be selected according to a purpose.

Examples of polymer films to which the cell sheets containing the myoblasts are attached include materials having cell adhesiveness based on physicochemical properties and materials having biochemical cell adhesiveness.

Examples of the materials having cell adhesiveness based on physicochemical properties include basic polymers such as hydrophilized polystyrene and polylysine, basic compounds such as aminopropyltriethoxysilane and N-(2-aminoethyl)-3-aminopropyltrimethoxysilane, and condensates containing them.

Examples of the materials having biochemical cell adhesiveness include fibronectin, laminin, tenascin, vitronectin, RGD (arginine-glycine-aspartic acid) sequence-containing peptides, YIGSR (tyrosine-isoleucine-glycine-serine-arginine) sequence-containing peptides, collagen, atelocollagen, gelatin, agarose, and mixtures thereof, e.g., matrigel, Pura-Matrix, fibrin, and the like. Furthermore, examples thereof include various kinds of glass, polystyrene and polypropylene subjected to plasma treatment, non-woven fabrics, paper, and the like. Especially, gelatin can be preferably used, and gelatin from porcine skin is particularly preferably used. Cell sheets containing the above-described micro-patterned myoblasts can be stably transferred due to its excellent adhesive strength with myoblasts and low cytotoxicity.

A method for detaching cell sheets containing myoblasts from a polymer film for collecting cell sheets is not particularly limited if being a method by which cell sheets containing myoblasts can be stably detached. Examples of such methods include a method of detachment due to a difference from the adhesive strength of an adherend such as a transplantation target or another artificial tissue, and a method of removing the polymer film. For example, in a case in which the polymer film contains gelatin, the gelatin film is brought in contact with the cell sheets containing the myoblasts and is then allowed to be in the state of having temperature kept at culture temperature. The gelatin is melted by being warmed to around temperature suitable for culture, specifically into a range of 33° C. to 40° C., and can be removed from the cell sheets containing the myoblasts.

Layered cell sheets containing myoblasts in which each sheet has controlled orientations are obtained by layering the cell sheets containing the myoblasts (micro-patterned myoblast-containing cell sheets) with controlled orientations, obtained in such a manner as described above. In the case of detaching the cell sheets containing the myoblasts from a substrate using a polymer film, the layered cell sheets containing the myoblasts may be obtained by layering the cell sheets containing the myoblasts in the state of adhering to the polymer film and then warming, to thereby melt the polymer film.

By layering a cell sheet containing myoblasts with random orientations on a cell sheet containing myoblasts with controlled (unidirectionally aligned) orientations, the orientations of the cell sheet containing the myoblasts with the random orientations are changed according to the cell sheet containing the myoblasts with the controlled orientations, and therefore, layered cell sheets containing myoblasts having a region in which the orientations of myoblasts in each sheet are identical to each other can be obtained. Such cell sheets containing myoblasts having a region in which the orientations of myoblasts in each sheet are identical to each other are advantageous for forming muscle tissue such as a myotube. According to such a method, layered cell sheets containing myoblasts having a region in which the orientations of myoblasts in each sheet are identical to each other can be obtained only by using one cell sheet containing myoblasts with controlled orientations, and therefore, the method is advantageous. In this case, it is preferable to allow the orientations in each sheet to be identical by self-organization by culturing the layered cell sheets containing the myoblasts using a myoblast growth medium and to then induce their differentiation into myotubes using a differentiation-inducing medium.

When underneath a cell sheet containing myoblasts with controlled orientations, a cell sheet containing myoblasts having orientations of which the directions are different from the controlled orientations (for example, having perpendicular orientations) is placed, the orientations of the bottom cell sheet containing the myoblasts are changed according to the top cell sheet containing the myoblasts, and therefore, layered cell sheets containing myoblasts having a region in which the orientations of myoblasts in each sheet are identical to each other can be obtained. In this case, it is preferable to allow the orientations of each sheet to be identical by self-organization by culturing the layered cell sheets containing the myoblasts using a myoblast growth medium and to then induce their differentiation into myotubes using a differentiation-inducing medium.

In the case of inducing differentiation of each of cell sheets containing myoblasts to form myotubes and then layering the cell sheets, self-organization does not occur, and layered cell sheets in which the orientations of each cell sheet are maintained can be obtained. In this case, the layered sheets with orientations varying from one layer to another can be designed.

Layered cell sheets containing myoblasts may contain, between cell sheets having cell population containing myoblasts, vascular endothelial cells or nerve cells of which the orientations are identical to those of the cell population containing the myoblasts. The vascular endothelial cells or nerve cells may be isolated and cultured from a living body or may be induced from a stem cell such as an iPS cell.

Such layered cell sheets containing myoblasts in which vascular endothelial cells or nerve cells are sandwiched can be obtained, for example, by placing and culturing vascular endothelial cells or nerve cells on a cell sheet containing cell population containing myoblasts with controlled orientations, to thereby form a layer of the vascular endothelial cells or the nerve cells, and layering a cell sheet containing myoblasts thereon. Because the vascular endothelial cells or the nerve cells are oriented in directions identical to those of the myoblasts with the controlled orientations by being cultured on the myoblasts with the controlled orientations, the layered cell sheets containing the vascular endothelial cells or the nerve cells of which the orientations are identical to those of the cell population containing the myoblasts can be obtained.

In the cell sheet containing the myoblasts to be layered on the layer of the vascular endothelial cells or the nerve cells cultured on the myoblasts with the controlled orientations, the orientations may be in identical directions or may be random before layering. By forming the layer of the vascular endothelial cells or the nerve cells on the cell sheet containing the myoblasts with the controlled orientations and layering the cell sheet containing the myoblasts with the random orientations thereon, the orientations of the cell sheet containing the myoblasts with the random orientations are changed according to the cell sheet containing the myoblasts with the controlled orientations and thereby the layered cell sheets containing the myoblasts and the vascular endothelial cells or the nerve cells having a region in which the orientations of myoblasts in each sheet are identical to each other can be obtained.

Although the application purposes of the layered cell sheets containing the myoblasts described in the present invention are not limited, the layered cell sheets can be preferably used, for example, for medical transplantation and regenerative medicine for recovering muscle tissue damaged by injuries and diseases.

EXAMPLES

The present invention is described in more detail below based on examples, but the present invention is not limited thereto.

<Method>

Production of Micro-patterned Thermoresponsive Surface

An original procedure for producing a micro-patterned thermoresponsive surface has been reported (Biomacromolecules 12, 1414-1418 (2011)). Specifically, a PIPAAm brush was formed on a glass substrate by a surface-initiated reversible addition-fragmentation chain transfer (RAFT) polymerization method (Biomacromolecules 11, 1991-1999 (2010)), and a positive photoresist (OFPR-800 LB, 34 cp) (TOKYO OHKA KOGYO CO., LTD.) was then spin-coated on a surface of the PIPAAm brush for 30 seconds by a spin coater ACT-300D (ACTIVE) at 8000 rpm. Irradiation with ultraviolet rays was performed using a photomask (stripe widths: 50 µm/50 µm), the photoresist was then selectively removed in an irradiated region using a liquid developer (2.38% tetramethylammonium hydroxide solution) (NMD-3) (TOKYO OHKA KOGYO CO., LTD.), and the exposed reactive terminal DTB groups of the PIPAAm brush were converted into inactive maleimide groups to prevent further polymerization. The residual photoresist was removed with acetone, and a hydrophilic polymer PAcMo was then spatially selectively polymerized on a PIPAAm brush region having DTB in its terminal, to generate a micro-pattern including a PAcMo-b-PIPAAm block polymer brush and PIPAAm brush region (50 µm/50 µm stripe) (upper left of FIG. 1a). As a control, a glass substrate which had no micro-pattern of PAcMo on its surface and on which a PIPAAm polymer was grafted was prepared (lower left of FIG. 1a).

Cell Culture

Myoblasts of human skeletal muscle were cultured in a growth medium for myoblasts of skeletal muscle (SkGM-2: Lonza) on a tissue culture polystyrene (TCPS) dish in 5% $CO_2$ at 37° C. The patterned or non-patterned PIPAAm-grafted glass substrate (20×20 mm) produced as described above was put on the TCPS dish (having a diameter of 35 mm), and the myoblasts (passage: <5) were seeded at a density of $5 \times 10^4$ cells/cm$^2$ on the surface of the polymer brush. The adherent cells were cultured in 5% $CO_2$ at 37° C. until becoming confluent and were observed with a phase-contrast microscope using a microscope ECLIPSE TE2000-U (NIKON CORPORATION, Tokyo, Japan).

Formation of myotubes was achieved by culturing the myoblasts in a differentiation-inducing medium (DMEM/F12, 1:1, supplemented with 2% horse serum) for 5 days. All the reagents for cell culture were obtained from Lonza (Walkersville, Md., U.S.A.).

Manipulation and Layering of Cell Sheets

Gelatin gel was put on a myoblast sheet made on the PIPAAm-grafted surface, and they were incubated together at 28° C. for 30 minutes, to allow the gelatin gel to adhere to the myoblast sheet. Then, they were incubated at 20° C. for 30 minutes, and the myoblast sheet was detached from the surface of the substrate. The cell sheet was transferred together with the gelatin gel onto a new TCPS dish, and was further incubated in a medium at 37° C. in the dish, to melt the gelatin gel.

For layering cell sheets, a second harvested cell sheet was transferred to the other cell sheet. The cell sheets forming two layers were incubated at 28° C. for 30 minutes, to allow the two cell sheets to adhere to each other, and the sheets were then harvested together by decreasing the culture temperature (20° C.). They were transferred onto a new TCPS dish or glass substrate, were then further incubated at 28° C. for 30 minutes, and were incubated at 37° C. for 30 minutes, to thereby melt the gelatin gel.

To observe a sequential change in cell orientation after layering the cell sheets, the myoblasts in the bottom cell sheet were stained with Cell Tracker (registered trademark) Green (Invitrogen). The cell sheet of the myoblasts adhering to the patterned surface or the non-patterned surface was incubated in a serum-free medium containing the coloring agent (final concentration: 3 µM) for 15 minutes. After exchange with a fresh serum-containing medium, a cell sheet stained with Cell Tracker (registered trademark) Orange (Invitrogen) or a cell sheet that was not stained therewith was layered on the treated cell sheets by the same method as described above. In each case, the myoblast sheet with aligned orientation was put on the multilayered cell sheet construct.

Immunofluorescence Staining

The confluent cells were fixed in 4% paraformaldehyde in phosphate buffered saline (PBS) at 37° C. for 15 minutes, and were subjected to permeabilization treatment in 0.5% Triton X-100 in phosphate buffered saline at room temperature (RT) for 5 minutes. The fixed cells were blocked in 2% bovine serum albumin (BSA) in phosphate buffered saline at RT for 30 minutes. The cells were washed with phosphate buffered saline three times, and were then incubated in Alexa Fluor 568-conjugated phalloidin (Invitrogen, Carlsbad, Calif., U.S.A.) (diluted 1:200 in BSA-phosphate buffered saline) at RT for 1 hour. For MHC staining, the cells were treated with a fluorescein-conjugated mouse anti-human MHC antibody (1:50) (R&D Systems, Inc., Minneapolis, Minn., U.S.A.) at RT for 1 hour. To observe fibronectin, the cell sheets were treated with an anti-fibronectin antibody (Abcam, Cambridge, Mass., U.S.A.), and were then treated with a second antibody labelled with Alexa Fluor 488 (Invitrogen). The images of the fluorescently stained cells were acquired by a confocal laser scanning microscope (LSM510; Oberkochen, Carl Zeiss Oberkochen, Germany).

To evaluate the alignment, lengths, and diameters of the myotubes, the immunofluorescence images of the MHC-positive myotubes were taken under three representative visual fields at 40- and 200-fold magnifications, and all data were represented as average value±standard deviation (n=5). For myotube orientation, a value of 0° shows alignment parallel to the axis of the stripe pattern, while a value of 90° represents alignment perpendicular thereto. Statistical significance was calculated by Student's t-test.

<Results>

To control the orientations of the myoblasts, hydrophilic poly(N-acryloylmorpholine) (PAcMo) was spatially selectively grafted on the surface of the thermoresponsive PIPAAm brush using a conventional photolithography technology. As a result, stripe patterns (50 µm) in two different polymer regions were formed on the surface (FIG. 1a).

Myoblasts of human skeletal muscle were aligned on the micro-patterned surface by seeding the cells once. The cells recognized the difference of cellular affinities between the two different regions, and as a result, were spread in the same directions as those of the stripe patterns of the PIPAAm and PIPAAm-b-PAcMo brushes. Furthermore, the aligned myoblasts became confluent while maintaining their cell sequences.

By decreasing temperature, the single cell sheet of the aligned myoblasts was detached from the surface on which PIPAAm was grafted (FIG. 1b). The cell sheet can be harvested and transferred using a stamp put on the cell sheet and coated with gelatin gel. The transferred myoblasts remained well aligned even on an ordinary tissue culture polystyrene (TCPS) dish for at least 3 weeks after the transfer (FIG. 1c).

Figure 2:
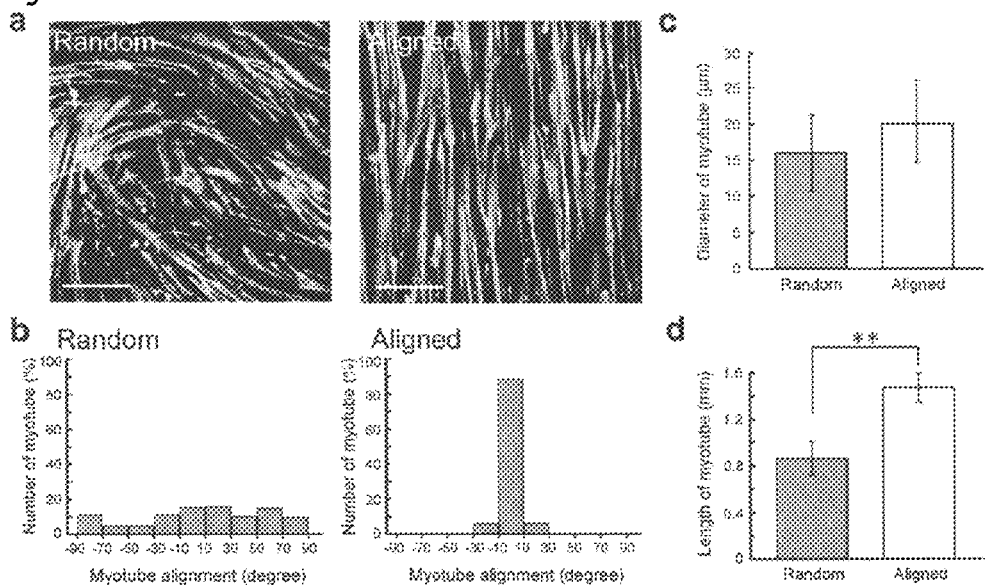
FIG. 2 shows views illustrating myotubes formed by transferring an aligned myoblast sheet to an ordinary cell culture dish and then culturing the aligned myoblast sheet. (a) Confocal microscope images (photographs) of myotubes after transfer of cell sheets from a patterned thermoresponsive surface (aligned) and a non-patterned thermoresponsive surface (random). After the transfer, the myoblast sheets were incubated in differentiation-inducing media for 5 days, and myosin heavy chains were stained with fluorescein. Scale bar: 200 μm. (b) The distributions of the alignment of myotubes in cell sheets obtained by being detached from patterned surfaces (aligned) and non-patterned surfaces (random) (n=5), by being transferred to dishes, and then cultured. (c, d) Views showing the diameters and lengths of the myotubes in the cell sheets including randomly oriented myoblasts (random) and aligned myoblasts (aligned) (**$p<0.01$) (n=5).
Figure 6:
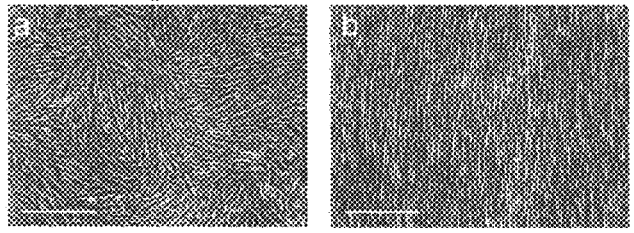
FIG. 6 shows photographs illustrating formation of myotubes in myoblast sheets transferred to cell culture dishes. The myoblast sheets were transferred from non-patterned surfaces (a and c) or micro-patterned (b, d, and e) surfaces, and then subjected to culture-incubation in myoblast growth media (a and b) or differentiation-inducing media (c to e) on the TCPS dishes for 5 days. Scale bar: (a to d) 500 μm, and (e) 100 μm.
Figure 6:
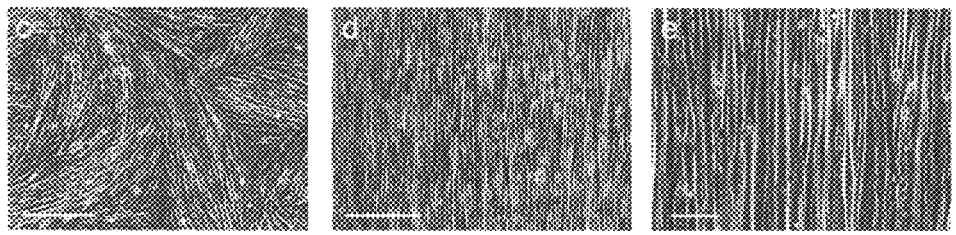

To start their differentiation into myotubes, the transferred myoblast sheet was cultured in a differentiation-inducing medium (2% horse serum-containing DMEM/F12 (1:1) medium). Although no difference in cellular orientation was observed, the form of it was microscopically obviously changed by culturing it in the differentiation-inducing medium (FIG. 6). As is clear from the myosin heavy chain (MHC)-stained image, the aligned myoblasts were efficiently differentiated into myotubes, and these cells remained well aligned even on an ordinary culture dish (FIGS. 2a and 2b). The diameters of the myotubes were not greatly different between the groups of the aligned myoblasts (Aligned) and the randomly oriented myoblasts (Random) (FIG. 2c), while the lengths of the myotubes were markedly increased by controlling the alignment of the myoblasts (FIG. 2d).

Figure 3:
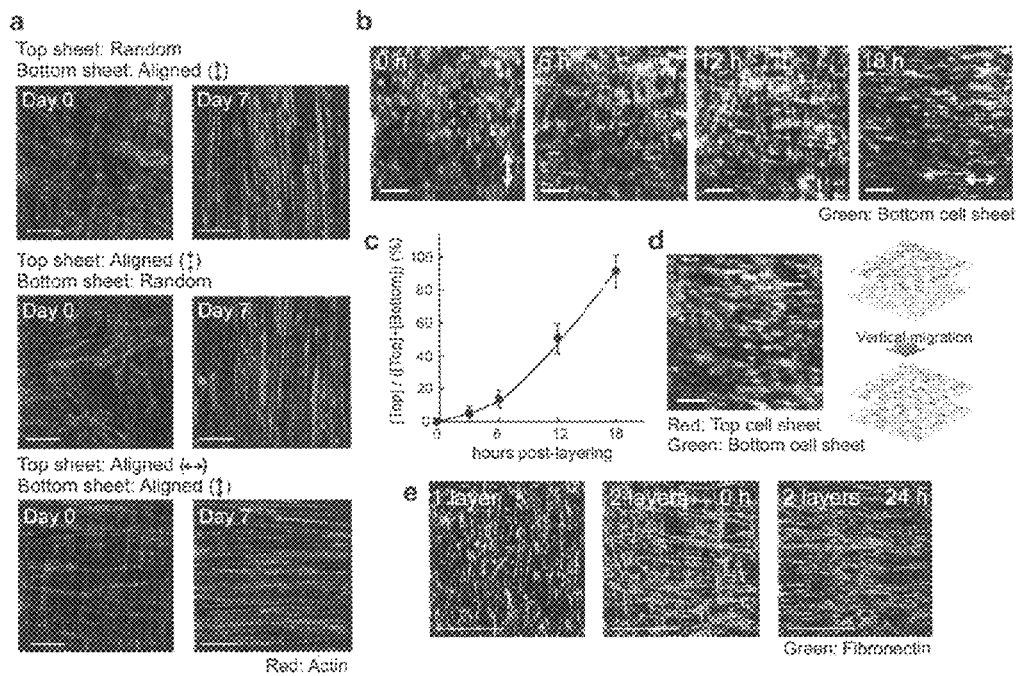
FIG. 3 shows views illustrating orientation in cell sheets forming two layers. (a) Confocal microscope images (photographs) of layered myoblast sheets forming two layers including a randomly oriented myoblast sheet and an aligned myoblast sheet. Two myoblast sheets produced on a non-patterned surface (random) and/or a patterned surface (aligned) were layered using stamps coated with gelatin gel, and were incubated for 7 days. Actin filaments were stained with Alexa Fluor 568 just after layering the cell sheets or 7 days after the layering. Fluorescence images (photographs) of a bottom aligned cell sheet after lapses of 0, 6, 12, and 18 hours following perpendicular layering of the aligned myoblast sheet (b), and the results of realignment analysis (n=5) (c). (d) A fluorescence image (photograph) of myoblast sheets forming two layers stained with Cell Tracker (registered trademark) Green and Cell Tracker (registered trademark) Orange after a lapse of 24 hours following layering. (e) Confocal microscope images (photographs) of fibronectin correlated with aligned cell sheets. The two aligned myoblast sheets were perpendicularly layered, and fluorescent-stained after a lapse of 0 or 24 hours following the layering. Scale bar: 100 μm.

A myoblast sheet with random orientation (random sheet) and a myoblast sheet with aligned orientation (aligned sheet) were layered utilizing a stamp coated with gelatin gel. The orientation of the randomly oriented myoblasts was changed when the randomly oriented myoblasts were layered on the aligned sheet, and the cells in themselves were finally aligned in the same directions as those of the layered aligned sheet regardless of the top or bottom cell sheet (FIG. 3a; upper column and middle column). As a result, all the myoblasts in the myoblast sheets forming two layers were aligned in the same directions as those of the aligned cell sheet.

Then, two aligned myoblast sheets were perpendicularly layered. Interestingly, the myoblast orientation of the bottom sheet was changed according to the orientation of the top sheet (FIG. 3a; lower column). To sequentially observe this behavior, only the bottom cell sheet was fluorescently stained, and the unstained aligned cell sheet was then layered perpendicularly on the stained cell sheet. Actually, this behavior rapidly occurred within about 24 hours, and the orientation of about half of the bottom cells was realigned after a lapse of 12 hours following the layering (FIGS. 3b and 3c). In addition, in the self-organized myoblast sheets forming the two layers, the cells forming the top and bottom cell sheets transferred between the sheets as illustrated in FIG. 3d, and were not able to be thus divided. Fibronectin existing as ECM was oriented in a manner similar to that of the myoblasts and was related closely to a change in cell orientation. Specifically, fibronectin in the bottom cell sheet was also realigned by layering with the aligned cell sheet according to a change in the cell orientation of the cell sheets forming the two layers (FIG. 3e).

Figure 4:
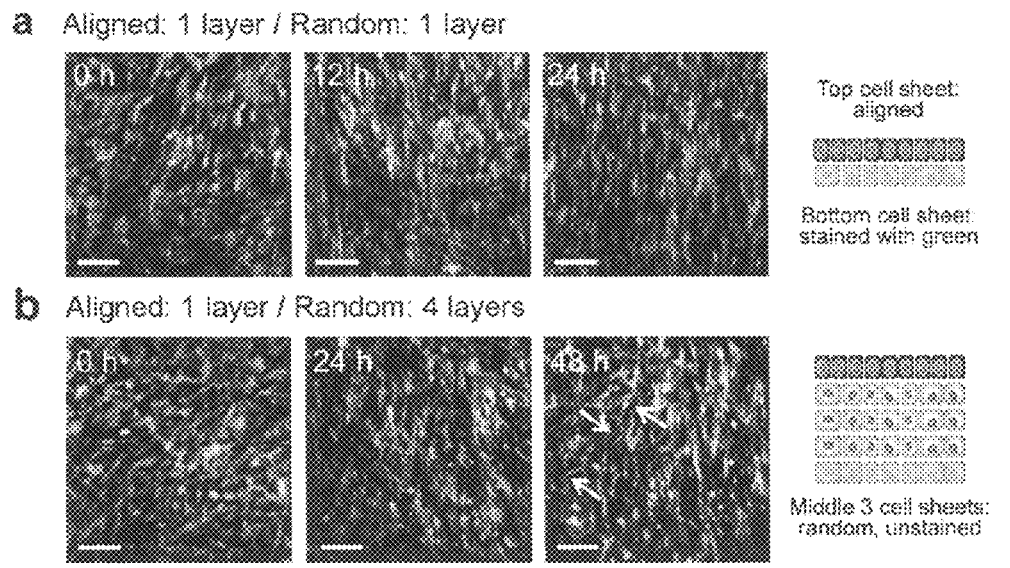
FIG. 4 shows views showing change in orientation in a layered product including multilayered myoblast sheets. The bottom cell sheet was stained with Cell Tracker (registered trademark) Green. Scale bar: 100 μm. (a) Photographs showing the results of layering an aligned sheet on one fluorescent-stained random sheet. (b) Photographs showing the results of layering three random sheets on a fluorescent-stained random sheet and then putting an aligned sheet on the four layered random sheets. Several cells were still randomly oriented after a lapse of 48 hours following layering (indicated by the white arrows).

Such self-organization behavior was also observed in myoblast sheets forming several layers. For example, three random sheets were put on one stained random sheet, and an aligned sheet was then layered on the four layered random sheets. Although the three cell sheets existed between the top aligned sheet and the bottom random sheet, the majority of cells in the bottom sheet had self-organized orientation and were aligned in the same directions as those of the top alignment cell sheet (FIG. 4b). In comparison with two layered cell sheets (FIG. 4a), the addition of the three random sheets caused the change in the orientation of the bottom sheet to be delayed, and some cells in the bottom sheet still had random orientation after a lapse of 24 hours following the layering. Furthermore, a few cells had random orientation even after a lapse of 48 hours following the layering (FIG. 4b).

Figure 5:
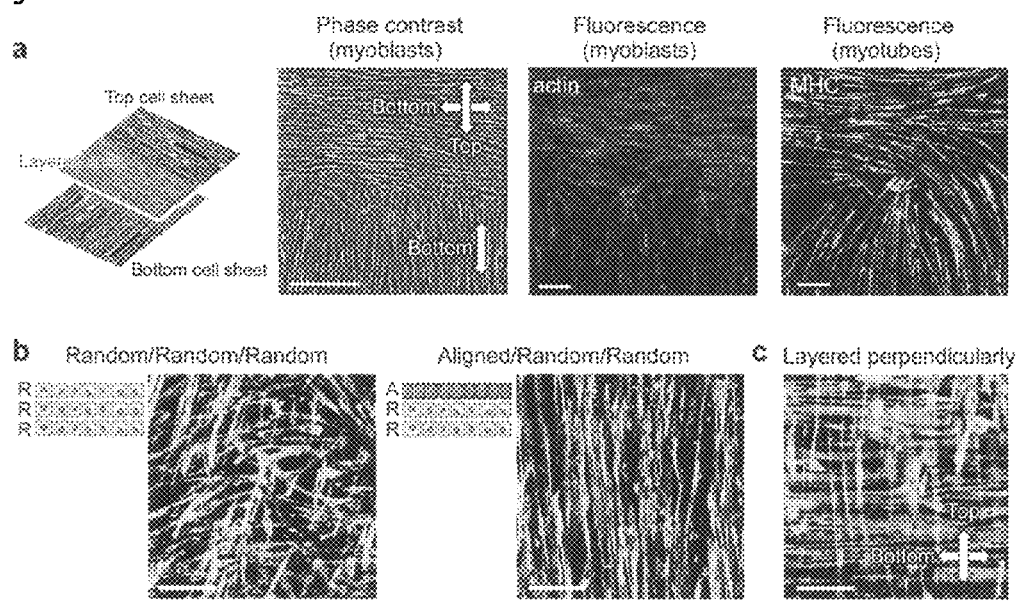
FIG. 5 shows views illustrating the construction of the formation of aligned myotubes through a process of self-organization of a cell sheet. Scale bar: 200 μm. (a) Photographs showing the results of layering an aligned cell sheet only on a half region of another aligned myoblast sheet and staining actin filaments with Alexa Fluor 568 after 24 hours, and showing the results of further culturing the layered myoblast sheets in differentiation-inducing media for 5 days and then fluorescent-staining myosin heavy chain (MHC) positive myotubes. (b) A photograph showing the result of layering one aligned sheet on two random sheets and then incubating the sheets in a growth medium for 2 days (aligned/random/random). As a control group, three random sheets were layered together (random/random/random). (c) A photograph showing the result of individually culturing two aligned cell sheets in differentiation-inducing media for 5 days and then perpendicularly layering the two cell sheets through a cell sheet layering process.

The self-organization behavior found in this research enables occurrence of peculiar formation of myotubes. When two aligned sheets are partially layered as illustrated in FIG. 5a, the cell orientation of the bottom sheet is changed and aligned with the top sheet. This occurred only in a region coming in contact with the top sheet. It was confirmed from the three-dimensional confocal image that the actin filaments of cell sheets forming two layers were aligned in two different directions (FIG. 5a). By culturing this myoblast construct in a differentiation-inducing medium, a myotube construct having two-dimensionally varying alignment was able to be created.

This self-organization behavior was useful for making a well aligned myotube construct including a plurality of cell sheets. When layered on two random sheets, one aligned sheet changed the myoblast orientation of the bottom, to finally allow all the myotubes of the cell sheets forming three layers to be well aligned in the same direction (FIG. 5b). In other words, one aligned myoblast sheet was enough to make an aligned myotube construct from a plurality of cell sheets.

On the other hand, 3D perpendicular orientation myotube formation was also enabled by layering two aligned myoblast sheets. First, myotubes were formed by culture in a differentiation-inducing medium, and an aligned myotube construct was then perpendicularly layered using a cell sheet layering process. Because the orientations of the myotubes were maintained according to their design, the perpendicularly different orientations were able to be also made by layering the aligned cell sheets (FIG. 5c).

Introduction of Vascular Endothelial Cells

A patterned PIPAAm-grafted glass substrate (20×20 mm) was put on a TCPS dish (having a diameter of 35 mm), and myoblasts of human skeletal muscle (passage: <5) were seeded at a density of $5 \times 10^4$ cells/cm$^2$ on the surface of the polymer brush. The myoblasts were cultured in a growth medium (SkGM-2: Lonza) in 5% $CO_2$ at 37° C. until becoming confluent to produce an orientation-controlled-type myoblast sheet. Then, vascular endothelial cells (HUVECs) from human umbilical vein pre-stained with Cell Tracker were seeded at a density of $5 \times 10^4$ cells/cm$^2$ on the orientation-control-type myoblast sheet. The HUVECs were cultured for around 3 hours to 1 day and confirmed to sufficiently adhere onto the myoblast sheet, another orientation-control-type myoblast sheet was then collected by a gelatin gel stamp, and the HUVECs were layered to be sandwiched between the two myoblast sheets and were cultured in a vascular endothelial growth medium. A fluorescence image before layering the other orientation-control-type myoblast sheet is shown in the upper left of FIG. 7, and a fluorescence image after the layering is shown in the lower left of FIG. 7.

Figure 7:
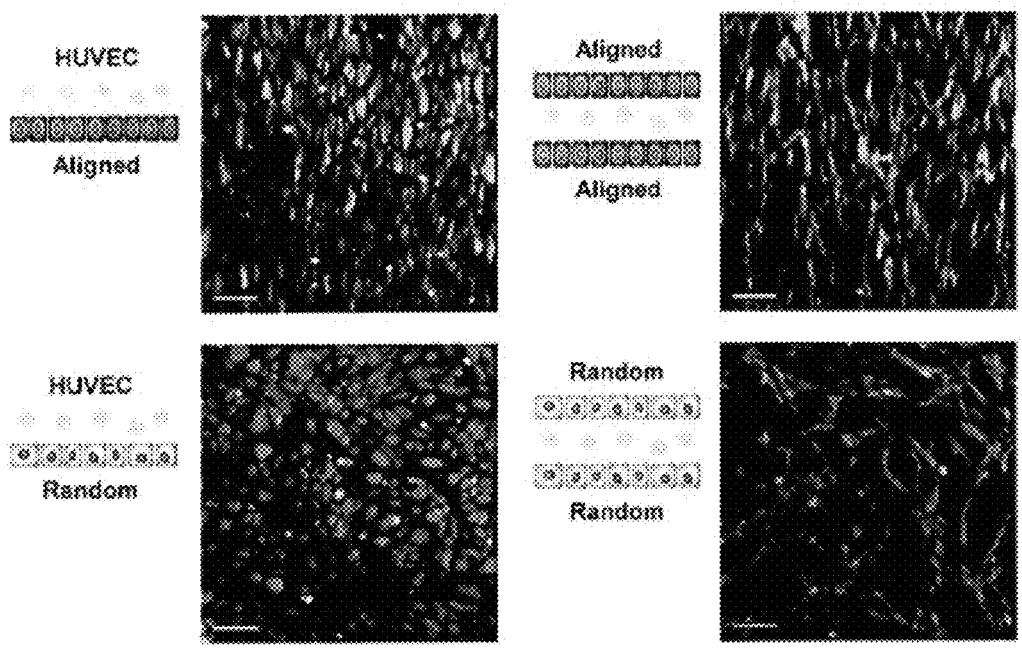
FIG. 7 shows views (photographs) showing the results of staining HUVEC cultured on myoblast sheets. The scale bars indicate 100 μm.

As a control, an HUVEC layer was formed on a myoblast sheet with random orientations (lower left of FIG. 7), and another myoblast sheet with random orientations was produced thereon (lower right of FIG. 7).

As a result, it was found that the vascular network structure of the HUVECs was formed in the same direction as those of the myoblasts when the cell layer of the HUVECs was sandwiched between the orientation-controlled-type myoblast sheets.

Figure 8:
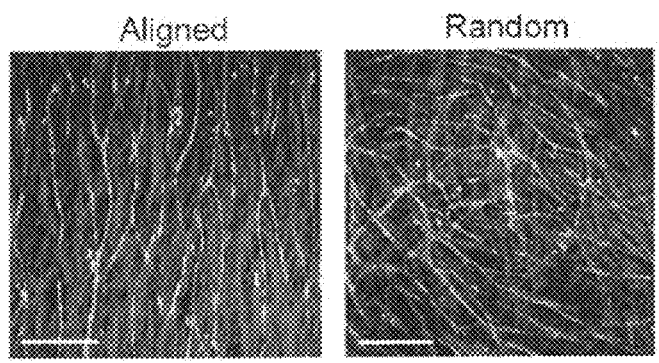
FIG. 8 shows views (photographs) showing the results of double-staining HUVEC cultured on myoblast sheets. The scale bars indicate 200 μm. Green shows HUVEC, and red shows actin.

The produced tissue obtained by layering the cell sheets was cultured in a vascular endothelial growth medium for 7 days, followed by fixing the cells with paraformaldehyde, allowing the HUVECs to react with fluorescently labeled Ulex Europaeus Agglutinin-1 (UEA-I) and to be stained in green, and allowing the actin of the myoblasts to react with fluorescently labeled phalloidin and to be stained in red. The results are illustrated in FIG. 8. The directions of the vessels were ununiform in the case of the sandwich between the myoblast sheets with the random orientations whereas the vascular network structure of the HUVECs was formed in the same direction as those of the myoblasts in the case of the sandwich between the orientation-controlled-type myoblast sheets.

Introduction of Nerve Cells

A patterned PIPAAm-grafted glass substrate (20×20 mm) was put on a TCPS dish (having a diameter of 35 mm), and myoblasts of human skeletal muscle (passage: <5) were seeded at a density of $5\times10^4$ cells/cm$^2$ on the surface of the polymer brush. The myoblasts were cultured in a growth medium (SkGM-2: Lonza) in 5% $CO_2$ at 37° C. until becoming confluent to produce an orientation-control-type myoblast sheet. Then, nerve cells differentiated from a human iPS cell (iCell Neurons, manufactured by Cellular Dynamics international) were seeded at a density of $1\times10^3$ to $2\times10^4$ cells/cm$^2$ on the orientation-control-type myoblast sheet. The nerve cells were cultured for 24 hours and confirmed to sufficiently adhere onto the myoblast sheet, another orientation-control-type myoblast sheet was then collected by a gelatin gel stamp, and the nerve cells were layered to be sandwiched between the two myoblast sheets and were cultured in a nerve cell growth medium for 5 days. Then, the cells were fixed with paraformaldehyde, and nerve cell marker neurofilament and myoblast marker desmin were stained using antibodies in red and green, respectively. The results are illustrated in the left of FIG. 9.

Figure 9:
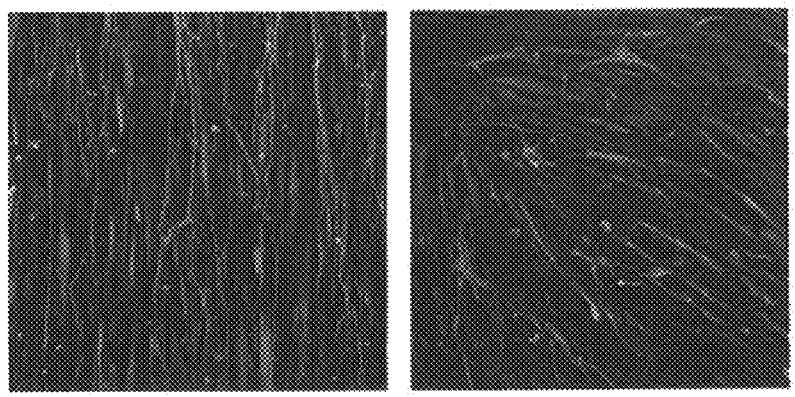
FIG. 9 shows views (photographs) showing the results of double-staining nerve cells cultured on myoblast sheets. The scale bars indicate 100 μm. Green shows desmin, and red shows neurofilament.

As a control, a nerve cell layer was formed on a myoblast sheet with random orientations, and another myoblast sheet with random orientations was produced thereon (right of FIG. 9).

As a result, it was found that a neural network structure was formed in the same direction as those of the myoblasts when the nerve cell layer was sandwiched between the orientation-control-type myoblast sheets.

INDUSTRIAL APPLICABILITY

The utilization of the present invention enables layered cell sheets containing myoblasts with controlled orientations to be efficiently obtained and is useful in the fields of regenerative medicine and the like.

What is claimed is:

1. Layered cell sheets, comprising a plurality of cell sheets in a layered configuration, wherein each cell sheet comprises a cell population containing myoblasts with a controlled orientation, wherein the layered cell sheets comprise a region in which an orientation of the cell population containing the myoblasts in each cell sheet is identical to each other, and wherein the layered cell sheets comprise vascular endothelial cells or nerve cells between the cell sheets comprising the cell population containing the myoblasts, and wherein the vascular endothelial cells or nerve cells have an identical orientation to the cell population containing the myoblasts.

2. The layered cell sheets according to claim 1, wherein each cell sheet comprising the cell population containing the myoblasts is obtained by culturing the myoblasts on a thermoresponsive polymer-coated substrate and by detaching the myoblasts from the substrate.

3. The layered cell sheets according to claim 1, wherein the percentage of cells in each cell sheet that are myoblasts is 50% or more.

4. The layered cell sheets of claim 1, wherein the controlled orientation is a unidirectional orientation.

5. The layered cell sheets of claim 1, wherein each of the vascular endothelial cells or nerve cells and the cell population containing myoblasts is in a unidirectional orientation.

6. The layered cell sheets of claim 1, wherein the vascular endothelial cells or nerve cells are cultured on a first myoblast containing cell sheet and then covered with a second myoblast containing cell sheet.

7. A method for producing the layered cell sheets comprising myoblasts and vascular endothelial cells or nerve cells according to claim 1, said method comprising a step of forming a layer of vascular endothelial cells or nerve cells on a first cell sheet comprising a cell population containing myoblasts with a controlled orientation and layering a second cell sheet comprising myoblasts thereon, and thereby obtaining layered cell sheets which comprise a region in which an orientation of the cell population comprising myoblasts and an orientation of vascular endothelial cells or nerve cells in each cell sheet are identical.

* * * * *